(12) United States Patent
Fritsch et al.

(10) Patent No.: US 9,144,299 B2
(45) Date of Patent: Sep. 29, 2015

(54) METHOD AND DEVICE FOR PRODUCING A BRUSH HEAD SECTION FOR AN ORAL CARE DEVICE AND BRUSH HEAD SECTION PRODUCED BY SAID METHOD AND/OR SAID DEVICE

(71) Applicant: Braun GmbH (a German Corporation), Kronberg (DE)

(72) Inventors: Thomas Fritsch, Eppstein (DE); Christof Miltenberger, Neu-Anpach (DE); Stefan Scheurich, Triefenstein (DE); Michael Duemig, Kredenbach (DE); Uwe Tretrop, Frankfurt/Main (DE); Hermann Frey, Kronberg (DE); Joerg Kotitschke, Waldems (DE); Ulrich Stoerkel, Bad Nauheim (DE); Andreas Reuschenbach, Schwalbach (DE)

(73) Assignee: BRAUN GMBH, Kronberg (DE)

( * ) Notice: Subject to any disclaimer, the term of this patent is extended or adjusted under 35 U.S.C. 154(b) by 371 days.

(21) Appl. No.: 13/689,882

(22) Filed: Nov. 30, 2012

(65) Prior Publication Data

US 2013/0139337 A1 Jun. 6, 2013

(30) Foreign Application Priority Data

Dec. 2, 2011 (EP) .................................... 11009543

(51) Int. Cl.
*A46D 3/00* (2006.01)
*A46B 3/00* (2006.01)

(Continued)

(52) U.S. Cl.
CPC . *A46D 3/005* (2013.01); *A46B 3/00* (2013.01); *A46B 9/04* (2013.01); *A46B 9/06* (2013.01); *A61C 17/222* (2013.01)

(58) Field of Classification Search
CPC .......... A46D 3/005; A46D 3/00; B29C 45/162
USPC ...................... 15/167.1, 105; 300/21; 264/243
See application file for complete search history.

(56) References Cited

U.S. PATENT DOCUMENTS

| 2,630,601 A | 3/1953 | Schiffer et al. |
| 5,256,048 A | 10/1993 | Jacobs et al. |

(Continued)

FOREIGN PATENT DOCUMENTS

| DE | 815034 | 9/1951 |
| DE | 845933 B | 6/1953 |

(Continued)

OTHER PUBLICATIONS

PCT Search Report and Written Opinion dated Mar. 14, 2013, 13 pages.

*Primary Examiner* — Shay Karls
(74) *Attorney, Agent, or Firm* — Vladimir Vitenberg

(57) ABSTRACT

A brush head section for an oral care device is provided. The brush section includes an insert being made from a first thermoplastic material by injection-molding, at least one oral cleaning element and a cleaning element carrier consisting of a second thermoplastic material or a second thermoplastic mixture. The insert and the at least one cleaning element are partially embedded into the cleaning element carrier by overmolding and the cleaning element carrier at least partly engages behind the insert. The hardness of the second thermoplastic material is less than the hardness of the first thermoplastic material.

15 Claims, 9 Drawing Sheets

(51) Int. Cl.
  *A46B 9/04*  (2006.01)
  *A46B 9/06*  (2006.01)
  *A61C 17/22* (2006.01)

(56) References Cited

U.S. PATENT DOCUMENTS

| | | |
|---|---|---|
| 5,458,400 A | 10/1995 | Meyer |
| 5,474,366 A | 12/1995 | Strutt et al. |
| 6,402,494 B1 | 6/2002 | Lanvers |
| 6,463,615 B1 | 10/2002 | Gruber et al. |
| 6,695,414 B2 | 2/2004 | Meyer et al. |
| 6,862,771 B1 | 3/2005 | Muller |
| 7,240,390 B2 | 7/2007 | Pfenniger et al. |
| 7,823,243 B2 | 11/2010 | Hohlbein |
| 7,861,356 B2 | 1/2011 | Kunath et al. |
| 8,534,769 B2 | 9/2013 | Loetscher et al. |
| 8,585,153 B2 | 11/2013 | Ebner |
| 2003/0170339 A1 | 9/2003 | Ebner et al. |
| 2004/0032159 A1 | 2/2004 | Buckner et al. |
| 2004/0154112 A1 | 8/2004 | Braun et al. |
| 2006/0107478 A1 | 5/2006 | Boucherie |
| 2006/0236483 A1 | 10/2006 | Koi |
| 2010/0043165 A1 | 2/2010 | Juentgen et al. |

FOREIGN PATENT DOCUMENTS

| | | |
|---|---|---|
| DE | 3340122 A1 | 5/1985 |
| DE | 3535449 A1 | 4/1987 |
| DE | 19504332 A1 | 8/1996 |
| DE | 19600767 B1 | 12/1996 |
| DE | 19754762 C1 | 12/1998 |
| DE | 20013862 U1 | 11/2000 |
| DE | 10038536 A1 | 2/2002 |
| DE | 10116790 A1 | 10/2002 |
| DE | 20109749 U1 | 10/2002 |
| DE | 10123329 A1 | 11/2002 |
| DE | 10217527 A1 | 11/2003 |
| DE | 10221786 A1 | 11/2003 |
| DE | 20301634 U1 | 6/2004 |
| DE | 102007007118 A1 | 8/2008 |
| DE | 202008010183 U1 | 1/2010 |
| DE | 10029690 B4 | 2/2010 |
| DE | 19949772 B4 | 8/2010 |
| DE | 102009009034 A1 | 8/2010 |
| DE | 102009018961 A1 | 10/2010 |
| DE | 102009021482 A1 | 11/2010 |
| EP | 1603429 B1 | 8/2007 |
| EP | 2210521 A2 | 7/2010 |
| EP | 1486137 B1 | 10/2010 |
| WO | WO2010142098 A1 | 12/2010 |

FIG. 2
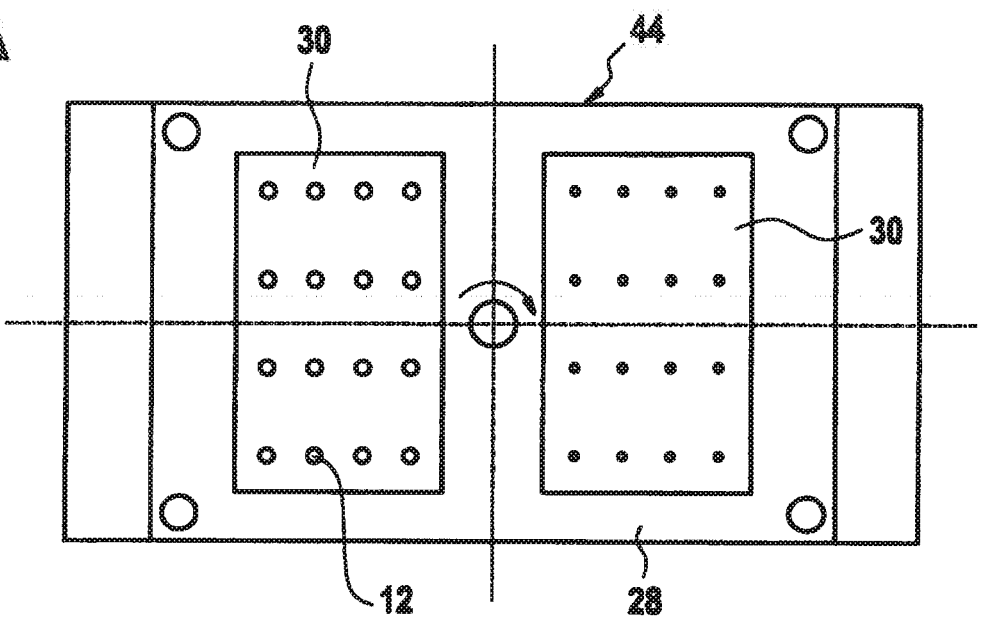
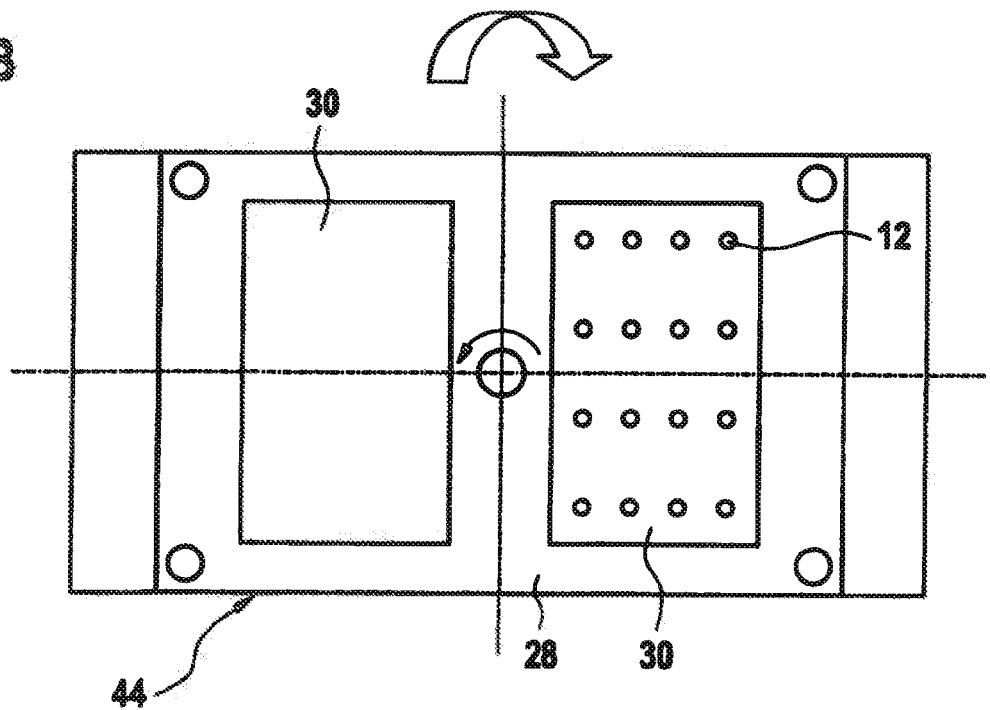

FIG. 7
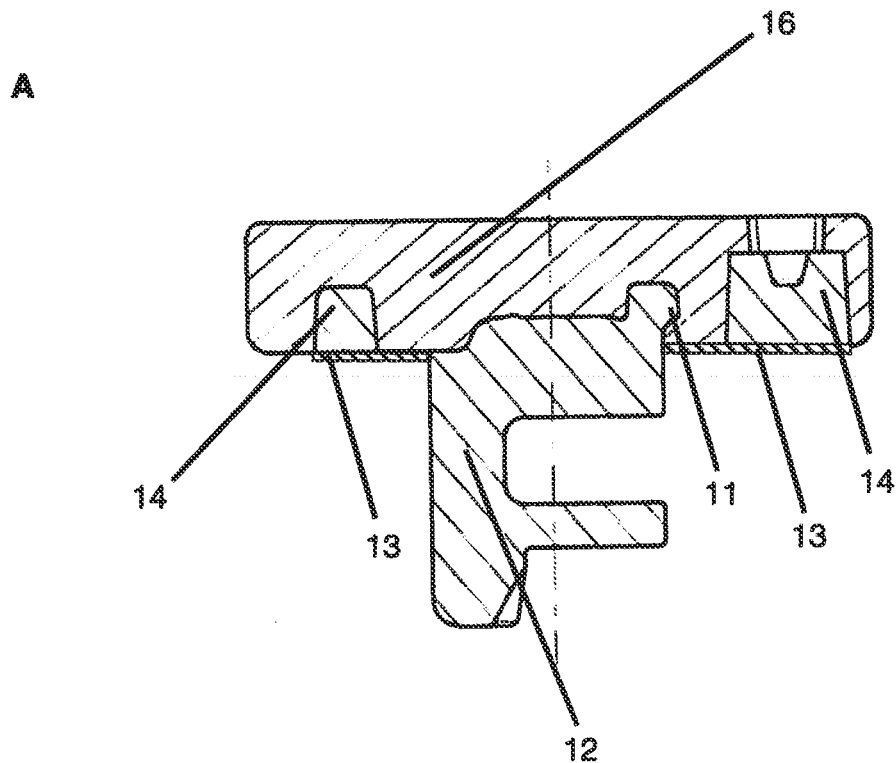
A
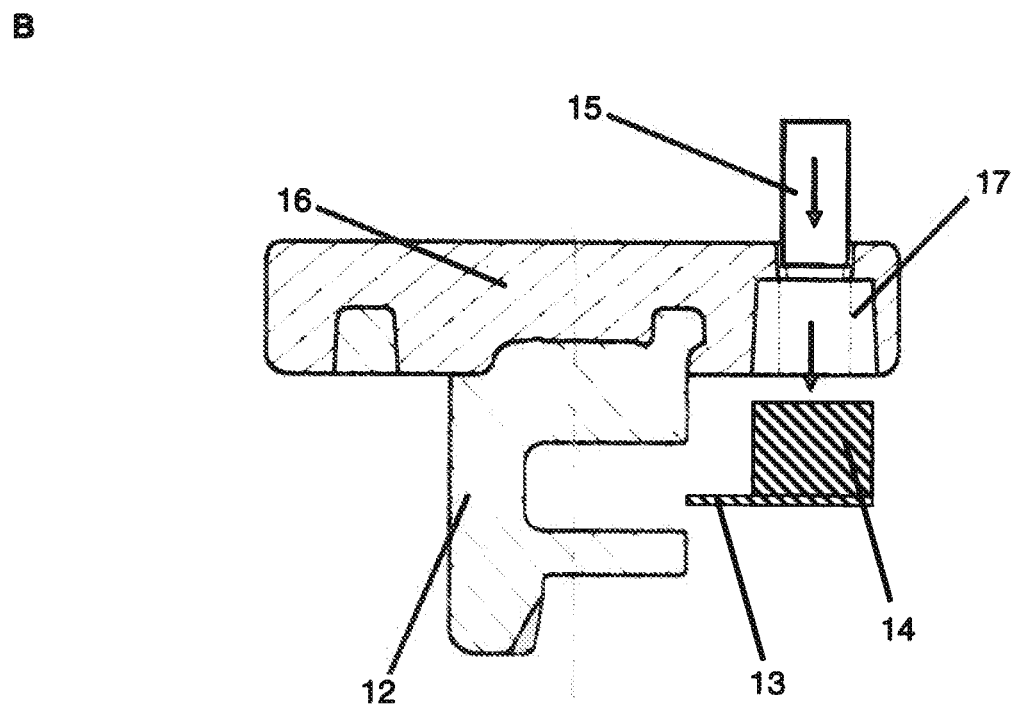
B

FIG. 8
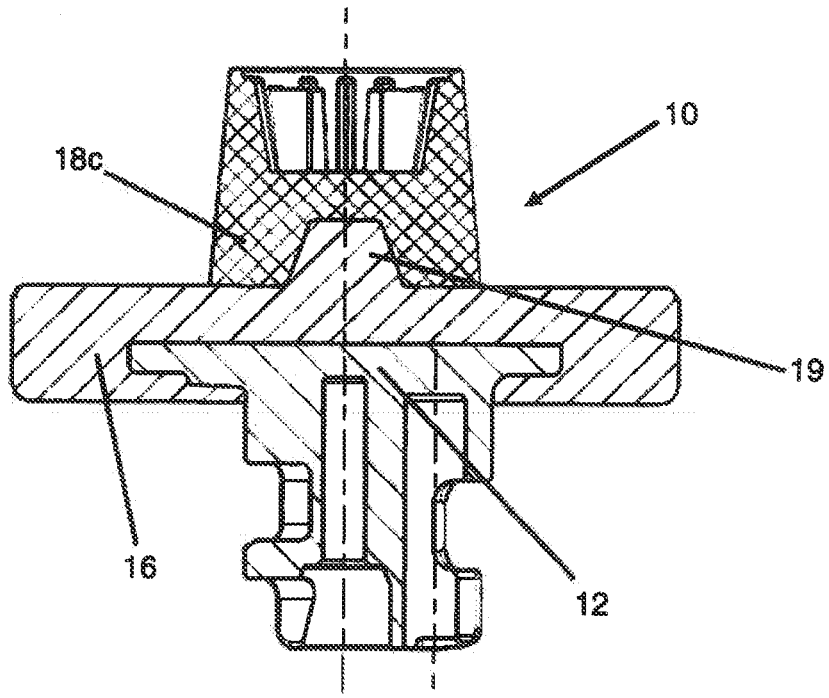
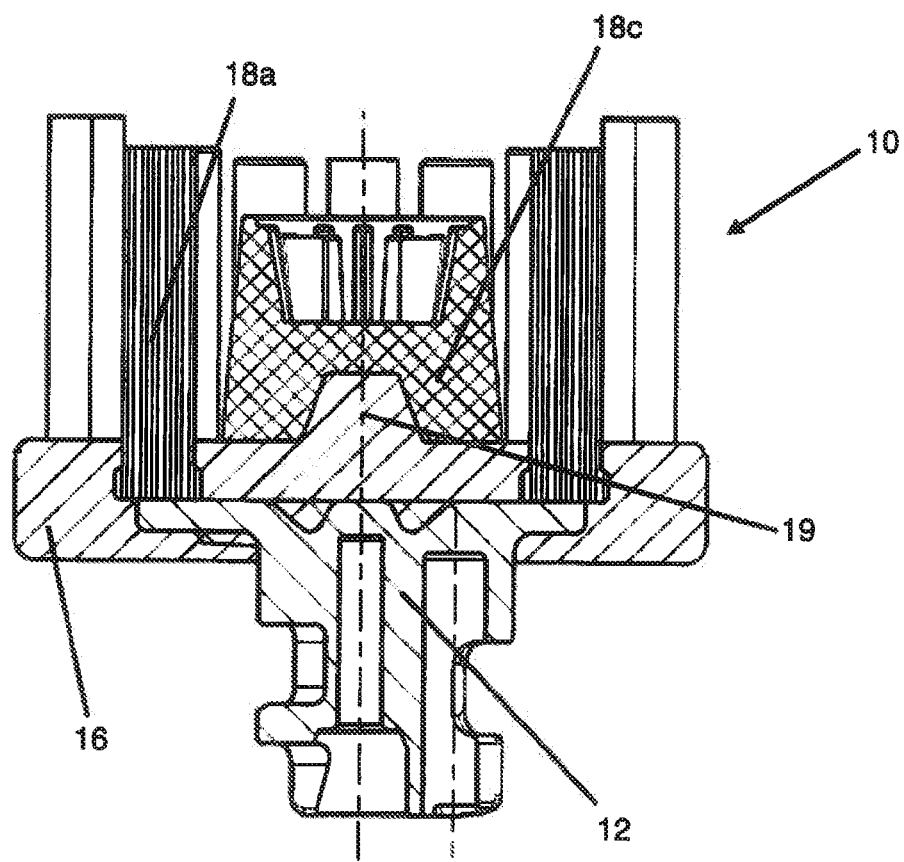

FIG. 9
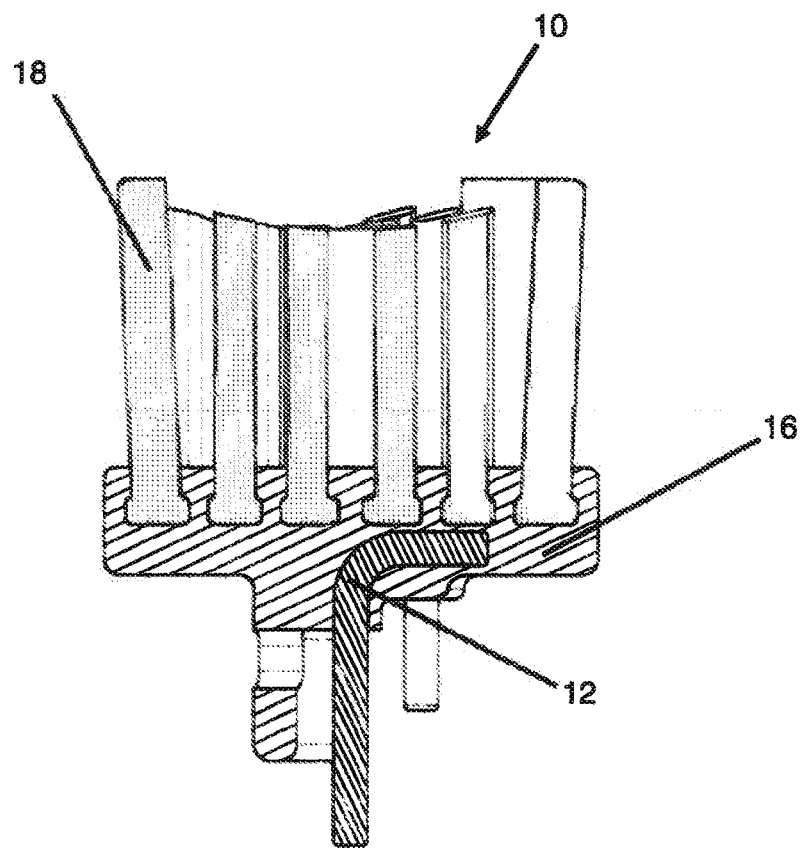
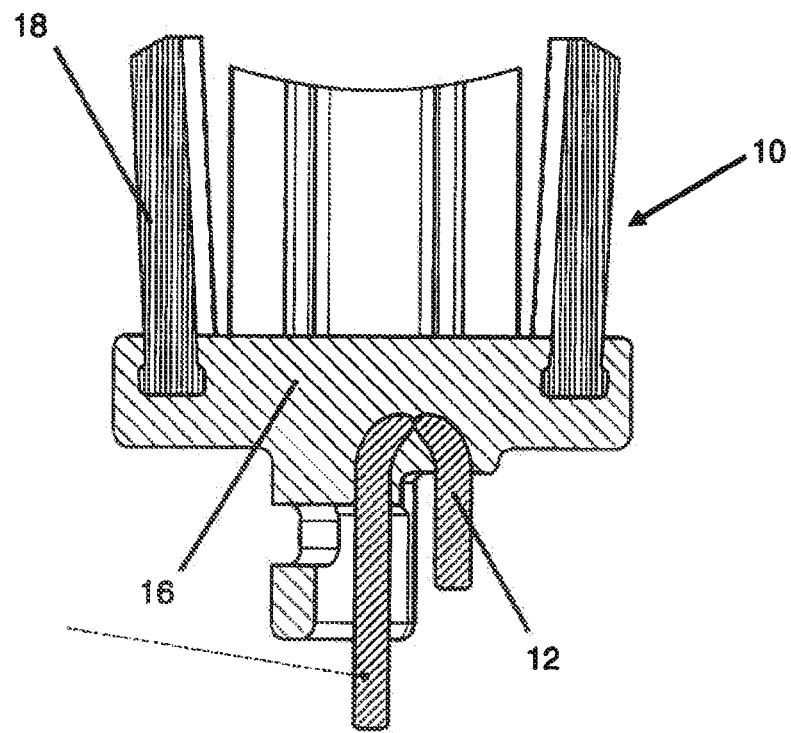

METHOD AND DEVICE FOR PRODUCING A BRUSH HEAD SECTION FOR AN ORAL CARE DEVICE AND BRUSH HEAD SECTION PRODUCED BY SAID METHOD AND/OR SAID DEVICE

FIELD OF THE INVENTION

There is provided a method for producing a brush head section for an oral care device. The present disclosure further relates to an injection molding device suitable to perform said methods. Further, there is disclosed a brush head section for an oral care device which may be producible by the disclosed method and using the disclosed device.

BACKGROUND OF THE INVENTION

It is known that brushes, in particular toothbrushes, comprise a brush head and a shaft or a handle. Individual bristle filaments are grouped together to form bristle bundles or bristle tufts which are arranged in a predefined geometry onto the brush head. The bristle tufts are fastened by anchors or anchor wires into blind ended tuft holes. Alternatively, anchor free or hot tufting methods are known to fasten the filaments to the brush head. According to the anchor free tufting method, the filament tufts are arranged in through-holes of a flat bristle carrier, so that the non-cleaning ends protrude over the bristle carrier plane. Then, the non-cleaning ends are molten to fasten the filament tufts durably to the bristle carrier and, finally, the carrier is mounted to the brush head, for instance, by ultrasonic welding. It is also known that filaments are arranged in a predefined bristle pattern, then, the filament ends of one tuft are fused and the fused tuft ends are over-molded by the thermoplastic used as material for the brush head and/or the handle. In comparison with anchor-tufted bristles, anchor-free tufting may result in a higher variability in bristle pattern or a more hygienic toothbrush surface. However, anchor free or hot tufting methods are so far mainly used for manual toothbrushes. The main problem is the higher material requirements for powered toothbrushes. Thus, it is an object of the present invention to provide an alternative anchor free or hot tufting method for the production of brush heads which can be used to produce both, manual and electric oral care devices.

SUMMARY OF THE INVENTION

In accordance with one aspect, there is provided a method for producing a brush head section for an oral care device comprising the following steps: injecting a first thermoplastic material into an insert-forming mold cavity to form an insert; transferring said insert into an over-molding mold cavity, wherein the insert is arranged partially inside and partially outside of said over-molding mold cavity; arranging one end of at least one cleaning element in said over-molding mold cavity, wherein the at least one cleaning element is arranged partially inside and partially outside of said over-molding mold cavity; injecting a second thermoplastic material into said over-molding mold cavity so that the part of the insert and the part of the at least one cleaning element which are located inside said over-molding mold cavity are over-molded by the second thermoplastic material, which second thermoplastic material thereby forms a cleaning element carrier, wherein the cleaning element carrier at least partly engages behind the insert and wherein the hardness of the second thermoplastic material is smaller than the hardness of the first thermoplastic material; and ejecting the resulting brush head section from said over-molding mold cavity.

In accordance with another aspect, there is provided a brush head section for an oral care device comprising an insert being made from a first thermoplastic material by injection-molding, at least one oral cleaning element and a cleaning element carrier consisting of a second thermoplastic material or a second thermoplastic mixture, wherein the insert and the at least one cleaning element are partially embedded into said cleaning element carrier by over-molding, wherein the insert is at least partly engaged behind by the cleaning element carrier material and wherein the hardness of the second thermoplastic material is smaller than the hardness of the first thermoplastic material.

In accordance with another aspect, there is provided a molding device comprising at least one insert-molding mold cavity and at least one over-molding mold cavity comprising at least one hot runner nozzle connected with said at least one over-molding mold cavity. The at least one insert-molding mold cavity and the at least one over-molding mold cavity have a common opening plane. Further the molding device comprises a transferring unit for transferring an insert molded in the insert-molding mold cavity to the over-molding mold cavity, comprising an index-plate suitable to be rotated by at least 180° and a rotation unit for rotating the index-plate. The molding device further comprises a first holding unit for fixing said insert in the at least one over-molding mold cavity, wherein the insert is arranged partially inside and partially outside of said at least one over-molding mold cavity, a second holding unit for fixing at least one cleaning element in the at least one over-molding mold cavity, wherein the at least one cleaning element is arranged partially inside and partially outside of said at least one over-molding mold cavity, and an ejecting unit to eject a molded brush head section from the molding device.

BRIEF DESCRIPTION OF DRAWINGS

These and other features will become apparent not only from the claims but also from the following description and the drawings, with the aid of which example embodiments are explained below.

FIG. 2 shows a top view of the inner side of the upper half 44 of the molding device 40; FIG. 2A shows the upper half 44 after the first injection molding step and FIG. 2B shows the upper half after rotating the transferring unit 28 and before performing the second injection molding step;

FIG. 7 shows a cleaning element carrier 16 having a recess 17 to carry further cleaning elements 18; FIG. 7A shows the cleaning element carrier 16 having at least one place holder element 14 and FIG. 7B shows the cleaning element carrier 16, wherein the place holder element 14 is ejected by a plunger 15 to achieve the recess 17;

FIG. 8A, 8B shows a cleaning element carrier 16 having a protrusion 19 to carry a further cleaning element 18c; FIG. 8A shows the cleaning element carrier 16 having only a central cleaning element 18c and FIG. 8B shows the cleaning element carrier 16, wherein two types of cleaning elements 18a, 18c are mounted therein; and FIG. 9A, 9B shows a cleaning element carrier 16, wherein the insert 12 is bearing shaft or a carrier spindle. FIGS. 9A and 9B show two different variants of the insert 12.

DETAILED DESCRIPTION OF THE INVENTION

Figure 1:
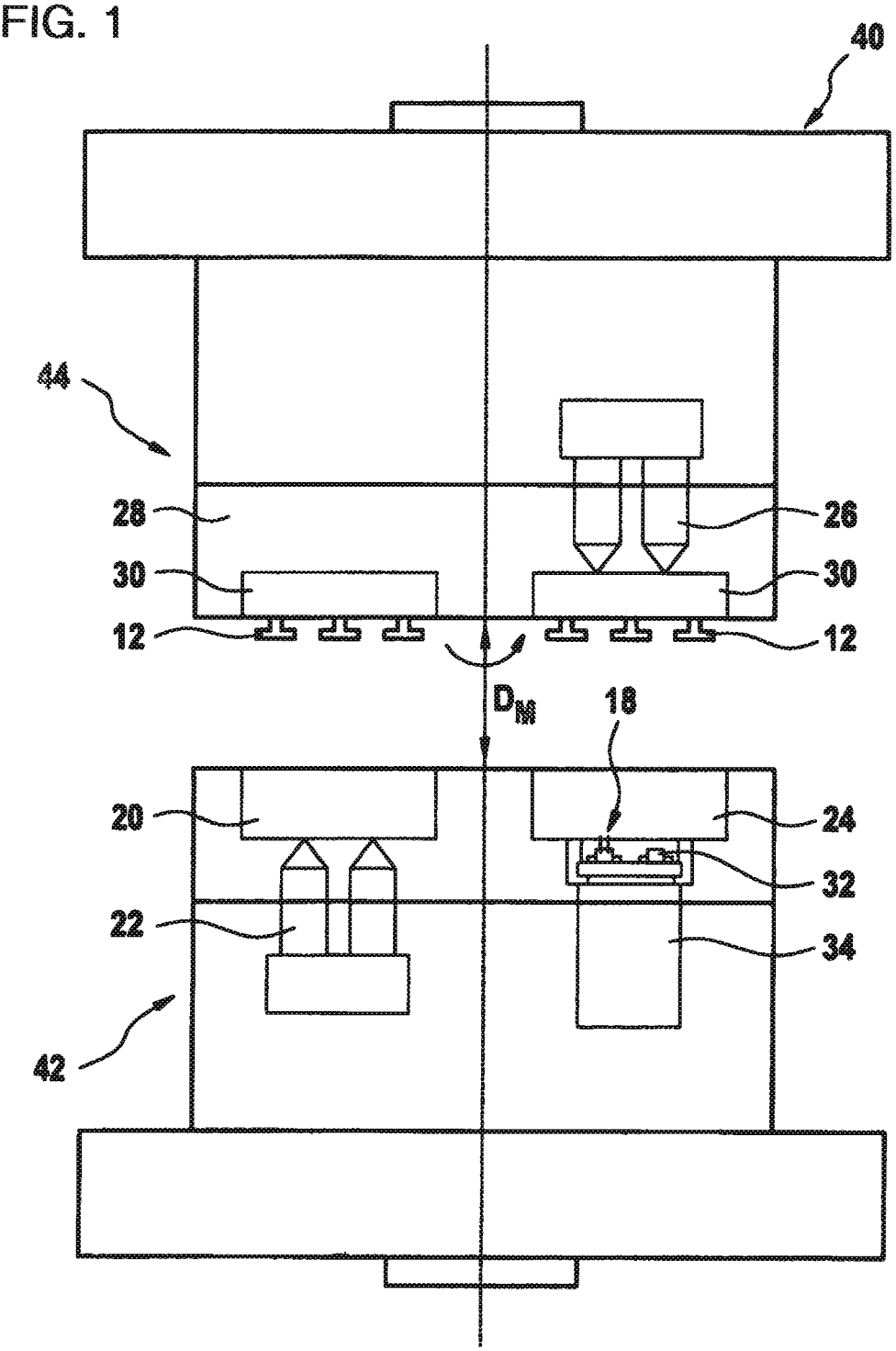
FIG. 1 shows a molding device 40 as disclosed herein as a side view, which molding device 40 comprises two halves 42, 44, a lower half 42 and an upper half 44.

The following is a description of numerous versions of a method for producing a brush head section for an oral care device. The description further discloses the brush head section produced and the molding device to perform said method. The description is to be construed as exemplary only and does not describe every possible embodiment since describing every possible embodiment would be impractical, if not impossible, and it will be understood that any feature, characteristic, structure, component, step or methodology described herein can be deleted, combined with or substituted for, in whole or in part, any other feature, characteristic, structure, component, product step or methodology described herein.

In accordance with one aspect of the disclosure, there is provided a method for producing a brush head section for an oral care device. Said brush head section shall comprise a higher precision component suitable for being used as part of a bearing or as a coupling component and cleaning elements safely mounted into the brush head section providing a smooth and hygienic surface. The oral care device may be, for example, a manual or an electric toothbrush. The method to provide such a brush head section comprises the step of providing an insert. Said insert may be provided by injecting a first thermoplastic material into an insert-molding mold cavity to form the insert and transferring said insert into an over-molding mold cavity. Thereby, the insert shall be arranged in such that it is located partially inside and partially outside of said over-molding mold cavity. In addition, at least one cleaning element is also arranged in the over-molding mold cavity, wherein the at least one cleaning element is arranged partially inside and partially outside of the over-molding mold cavity and the insert and the cleaning element are over-molded forming a cleaning element carrier.

"Partially inside and partially outside" as used herein shall mean that parts of the insert and/or the cleaning elements are located outside the hollow space of the mold cavity. "Hollow space of the mold cavity" as used herein shall mean the space covered by the inner surface of the mold cavity. Every part of the insert and/or the cleaning elements which is located inside of this inner surface shall be considered as being "inside" of the mold cavity. Every part of the insert and/or the cleaning elements which is located outside of this inner surface shall be considered as being "outside" of the mold cavity. Thus, being "outside" of the mold cavity does not mean being outside of the molding device.

After the insert and the at least one cleaning element are arranged in the over-molding mold cavity, a second thermoplastic material is injected into said over-molding mold cavity so that the part of the insert and the part of the at least one cleaning element which are located inside said over-molding mold cavity are over-molded by the second thermoplastic material, whereby the second thermoplastic forms a cleaning element carrier. "Over-molding" as used herein shall mean that the insert and the at least one cleaning element are at least partially embedded into the over-molding material. That means, that the insert is connected to the cleaning element carrier by positive fit, for example by forming one or more undercuts. In particular, the insert may at least partly be engaged behind by the cleaning element carrier (i.e. the cleaning element carrier at least partly engages behind the insert). For example, the insert may be a cylinder-like structure having a radially larger section (e.g. a disc-like structure having a larger diameter than the cylinder-like structure). The cleaning element carrier may then at least partially engage behind the radially larger section such that the insert is non-detachably connected to the cleaning element carrier even in cases where the first and second thermoplastic material do not chemically bond to each other in the over-molding step. The at least one cleaning element may be connected to the over-molding material by positive fit and by chemical bond. The first thermoplastic material is in particular different to the second thermoplastic material. In particular, for molding the insert a first thermoplastic material having a higher hardness compared to the hardness of the second thermoplastic material used for molding the cleaning element carrier can be used. The insert may in particular be arranged as a coupling part that couples the brush head section to a drive part for driving the brush head section into motion. The drive part may in particular be borne by a support structure of the insert and the drive part may move with respect the insert in order to drive it into motion. Hence, a hard first thermoplastic material may be used that can better withstand the abrasion caused the moving drive part. A softer second thermoplastic material may be chosen for the cleaning element carrier which will get in contact with the gums and other soft tissue during the intended use of the brush head section.

"Cleaning element carrier" as used herein shall mean a structural element which carries at least one cleaning element. According to the method disclosed herein, the cleaning element carrier partially embeds the at least one cleaning element and the insert. After forming the cleaning element carrier by injection molding, the cleaning element carrier can be ejected from the over-molding mold cavity. The brush head section may be used as it is manufactured in the molding device. In addition, the brush head section may be modified by further processing steps.

A coupling element or a part of a driving system of an electric toothbrush may be used as an insert which is provided according to the disclosed method in a first molding step. Said insert may be, for example, a drive part, a bearing, a bearing shaft, a carrier spindle or a security anchor. In addition, the insert may comprise at least a second insert. Suitable materials for a second insert may be metals or metal alloys. Thus, the molded insert might be a one component insert, a two or more component insert or may even be a multi-component part. For example, a pre-insert may be over-molded at least partially. The pre-insert may be for example a coupling element or a part of a driving system. Said pre-insert may be arranged partially inside the insert-molding molding cavity during the pre-molding step. In addition or alternatively, the insert may be over-molded to form, for example an elastomeric element. Over-molding can be performed in the insert-molding molding cavity before the insert is transferred to the over-molding molding cavity or in the over-molding molding cavity before the cleaning element carrier is molded. The elastomeric element may be, for example, a nub, a pin, a fin, a wall, a bar, a gutter, a curve, a circle, a textured element, a polishing element such as, for example, polishing cups or a tongue cleaning element or a combination thereof. Natural rubber, synthetic rubber, thermoplastic elastomers or a mixture thereof may be used as an elastomeric material to form the elastomeric elements.

A "textured element" as used herein, refers to a structure that has a macroscopic surface texture. For example, the textured element may be composed of a cluster of ribs, fins, columns, or other protrusions, or a combination of ribs, fins, columns, or other protrusions, that together form a unitary structure. In addition or alternatively, the texture can be imparted to the member by a manufacturing process such as injection molding, by embedding particles in the surface of the member, or by selecting a material for the member that inherently has a surface texture, e.g., an open cell foam.

Injection into the insert-molding and/or the over-molding mold cavity may be a hot runner injection. The insert-molding cavity and the over-molding cavity may be part of one or different molding devices. Injection into the insert-molding and the over-molding cavity may be performed from the same or from different sides of the injection molding device. For example, injection is performed from the ejection side of the molding device. The insert-molding and the over-molding mold cavities may be arranged in that the thermoplastic material can be injected substantially vertically relative to the ground upon the injection molding device is placed. The injection may be performed against gravity and/or in accordance with gravity. Alternatively, the insert-molding and over-molding mold cavities may be arranged in that the thermoplastic material can be injected substantially in parallel to the ground upon the injection molding device is placed. In addition, the thermoplastic material can be injected in any injection direction relative to the ground upon the injection molding device is placed, meaning that the injection direction may be angled to the ground. The thermoplastic material may be injected using a cold runner injection. Thermoplastic material which is injected into the insert-molding and the over-molding cavity might be the same material or different materials. According to the method as disclosed herein, the thermoplastic material may be injected substantially simultaneously. "Substantially simultaneously" as used herein shall mean that the thermoplastic material can be injected in parallel. For example, injection of both thermoplastics may start at the same time or injection may end at the same time. Alternatively, if injection time needed to inject one thermoplastic material is significantly shorter than injection time needed to inject the other thermoplastic, injection of the thermoplastic material which is injected faster may also start later and may end earlier.

In addition or alternatively, the transfer of the insert from the insert-molding mold cavity to the over-molding mold cavity may be performed automatically. For example, a part of the molding device may be used to transfer the insert. Alternatively, the insert may be transferred using a separate transferring unit. Using a part of the molding device may be helpful to meet geometrically requirements of the molding device. The insert can be transferred to the over-molding mold cavity by rotating a part of the molding device, for example, an index-plate or a part of the mold cavity, such as, for example, a part of the molding haves or a slide. Said rotatable part of the molding device may be on the ejection side of the molding device. The rotation may be in the opening plane of the molding device. That means, if the molding device is arranged horizontally, the rotation may be horizontal, if the molding device is arranged vertically, the rotation may be vertical and if the opening plane is angled to the ground the rotation may be in the same inclined plane. In particular, the part of the mold cavity and/or the index-plate may be rotated by at least 180° to transfer the insert form the insert-molding mold cavity to the over-molding mold cavity. During said transfer the insert may comprise a holding unit which is removably connected to the insert. The holding unit may be injection molded to the insert via a predetermined break point or the holding unit may comprise a grappler, picker, sucker etc. The holding unit may be a bar which can be picked up by the transferring unit. In addition or alternatively, the bar can be picked up by the index-plate. Alternatively, the insert which might be a drive part, a bearing shaft, a carrier spindle or a security anchor may be transferred directly to the over-molding mold cavity. Said transfer may be performed automatically for example, by using a part of the molding device or by using a separate providing unit. The insert may be located in a mold bar or it may be arranged in the molding device by a movable grappler, picker, sucker etc.

In addition or alternatively, the at least one cleaning element may be arranged in the over-molding mold cavity by a holding unit. Said holding unit may be suitable to fix a plurality of cleaning elements in a predefined pattern. A "pattern" as used herein shall include any horizontal arrangement of one or more kinds of cleaning elements as well as different angles of inclination relative to the vertical, different horizontal profiles or a combination thereof. A suitable holding unit may be, for example, a mold bar. "Mold bars" as used herein shall mean a mold having blind end holes, wherein the blind end holes are suitable to carry the at least one cleaning element at least partially and wherein the blind end holes are arranged in a pattern corresponding to the pattern of the cleaning elements in the brush head to be formed. Cleaning elements may be arranged in a mold bar in such that the ends of the cleaning elements which are intended to clean are located inside the mold bar and the ends which shall be mounted into the brush head are protruding from the mold bar. The mold bar may be arranged inside the molding device in such that the ends of the cleaning elements protruding from the mold bar are located inside of the over-molding mold cavity. The mold bar may locate the cleaning elements from the bottom of the cleaning device into the over-molding mold cavity. Several mold bars can be used to provide set of cleaning elements in more than one over-molding cavity. Preformed cleaning elements can be placed into the blind-holes of the mold bars or may be produced therein. For example, bristle elements may be preformed and placed into the mold bars. In addition or alternatively, elastomeric cleaning elements may be injected directly into the blind-holes of the mold bars.

The step of transferring the insert from the insert-molding mold cavity to the over-molding mold cavity or the step of arranging the insert partially inside of the over-molding mold cavity and the step of positioning the cleaning elements partially inside of the over-molding mold cavity may be performed successively. Alternatively, transferring of the insert to the over-molding mold cavity and arranging at least one cleaning element partially in the over-molding mold cavity can be performed simultaneously. That means, the index-plate may rotate transferring the insert to the over-molding mold cavity top-down, while a mold bar may be arranged from the bottom into the over-molding mold cavity. The insert may be arranged in the mold cavity using a grappler, a picker, a sucker, clamps, clips, squeezers, an adhesive element or another component which is able to arrange the insert in a predefined position. The insert may be arranged top-down, while a mold bar carrying the at least one cleaning elements may be arranged from the bottom into the mold cavity. Alternatively, the insert and the at least one cleaning element may be arranged in mold bars.

After injection molding of the cleaning element carrier which is formed in the over-molding mold cavity, the final brush head section comprising the insert, the cleaning element carrier and the at least one cleaning element is ejected from the molding device. Thereby, the brush head section may remain in the mold bar during ejection from the over-molding mold cavity. Thereby, the mold bar may be lowered until the mold bar can be extricated from the molding device and a new mold bar can be entered. After delivering the mold bar from the molding device, the brush head section can be cooled down finally. As the cleaning elements are located inside the mold bar, the insert is protruding from the cleaning element carrier to be handled easily. For example, the insert can be mounted to a driving rod. Further, it is possible to transfer the brush head section to further manufacturing steps via the mold bar. The brush head section may be processed further. One further processing step may be adding at least one additional cleaning element. For example, an elastomeric element may be injection-molded to the brush head section manufactured as described herein. Such an elastomeric element may be, for example, a nub, a pin, a fin, a wall, a bar, a gutter, a curve, a circle, a textured element, a polishing element such as, for example, polishing cups or a tongue cleaning element or a combination thereof. Natural rubber, synthetic rubber, thermoplastic elastomers or a mixture thereof may be used as an elastomeric material to form the elastomeric elements.

By performing one or more of the steps of the manufacturing method described above a brush head section for an oral care device can be produced. Thus, herein a brush head section for an oral care device is disclosed which is obtainable by a method as disclosed herein.

The method as described herein can be performed in parallel several times. That means that more than one insert is produced in the insert-molding injection molding step or more than one insert is provided and more than one cleaning element carrier is produced in the over-molding molding step. Parallel injection molding of multiple brush head sections made the method time-effective and cost-effective.

Herein, a brush head section for an oral care device is provided. Said brush head section may comprise an insert which may consist of a first thermoplastic material or a metal or a metal alloy may be over-molded with said first thermoplastic material, at least one oral cleaning element and a cleaning element carrier. Said cleaning element carrier consists of a second thermoplastic material which might be a different material compared to the first thermoplastic material used for the insert. For example, the second thermoplastic material may have a smaller hardness than the first thermoplastic material. The insert and the at least one cleaning element are partially embedded into said cleaning element carrier by over-molding so that the cleaning element carrier at least partly engages behind the. If two or more thermoplastic materials are used, for example, a first thermoplastic material which forms the insert and a second thermoplastic material which forms the cleaning element carrier, those thermoplastic materials may have different material properties to meet different requirements of the parts of the brush head to be formed. For example the first thermoplastic material used for the insert shall provide rigidity and/or stiffness. Further, its surface has to be formed precisely, if the insert represents a part of a bearing or a coupling element. The second thermoplastic material used for the cleaning element carrier should not enter into a cleaning element, for example a bristles tuft, during molding and this material should provide a good retention force to the insert and the cleaning element to be embedded. Suitable properties for distinction of two thermoplastics are, for example, Shore hardness, in particular Shore-A hardness or Shore-D hardness, melting point, melt flow index, viscosity in molten state, strength, hardness, rigidity, abrasion resistance, heat resistance and/or pressure during injection.

The hardness of the first thermoplastic material used for molding the insert may be higher than the hardness of the second thermoplastic material used for over-molding. In addition or alternatively, the first thermoplastic material used for the insert may also have a higher melting point, rigidity, strength, abrasion resistance and/or heat resistance and/or can be injected with a higher pressure than the second thermoplastic material used for over-molding the cleaning element carrier. In addition or alternatively, the first thermoplastic material of the insert may also have a lower viscosity in molten state or a lower melt flow index than the second thermoplastic material of the cleaning element carrier. If, the insert and the cleaning element carrier are made of different thermoplastic material materials, a suitable first thermoplastic material which can be used for molding the insert is polyoxymethylene (POM). In particular, polyoxymethylene is suitable to form parts of bearings showing a high rigidity and a precise surface. In addition or alternatively, the second thermoplastic material used to form the cleaning element carrier should be a material which does not enter into the blind holes of a mold bar.

Suitable second thermoplastic materials which can be used for over-molding and forming the cleaning element carrier can be, for example, polypropylene, polyethylene or polyethylene terephthalate.

The cleaning element carrier may be a flat body, for example a flat disk, wherein the cleaning elements, for instance bristle filaments, can be located at one side of the flat body and the insert may be located on the other side of the flat body. The insert may comprise at least one protrusion to form an undercut after being over-molded. Said protrusion which is partially embedded in the cleaning element carrier by at least a partial engagement of the cleaning element carrier behind the insert locks the insert in the cleaning element carrier securely by positive fit. It is noted that "engaging behind" shall not necessarily mean that the part of the cleaning element carrier that engages behind the insert fully envelopes the insert, but that it is sufficient that the insert has a section behind which the cleaning element carrier can engage (FIGS. 8A and 8B show one example embodiment). The insert may also be a flat body, for example a flat disc having a protrusion at one side. The flat disc may be over-molded completely so that only the protrusion protrudes from the cleaning element carrier after over-molding. The cleaning element carrier may be a plate having a round, an elliptic, an oval, an elongated, a polygonal shape, or a combination thereof. The thickness of the cleaning element carrier may be as small as possible, but the insert and the at least one cleaning element have to be fixed securely.

In addition or alternatively, the insert may be a part of a replacement brush head to be mounted onto an electric toothbrush handle, or a part of a manual toothbrush. The insert may be a coupling element, a part of a bearing, a bearing, a bearing shaft or a drive part connectable to a driving shaft of a replacement brush head. In addition or alternatively, the insert may be a part of a brush head, or a part of a neck or a part of a handle of a manual toothbrush. In addition or alternatively, the insert may be a tongue cleaner or a gum massaging element.

In addition or alternatively, the at least one cleaning element which is part of the brush head section according to the present disclosure, may be an elastomeric cleaning element, such as for example, elastomeric walls, elastomeric bars, elastomeric gutters, elastomeric curves, elastomeric circles, textured elements, elastomeric nubs, elastomeric fins, elastomeric pins polishing elements, such as, for example, polishing cups or a combination thereof. Alternatively, the at least one cleaning element may be a plurality of filaments or bristles, wherein the plurality of filaments may be arranged in round tufts, elliptic tufts, oval tufts, elongated polygonal tufts, or a combination thereof. The filament tufts may comprise one or more kinds of bristle filaments.

Suitable filament properties which may distinguish the filaments from each other may be filament material, filament length, filament diameter, filament elasticity, filament end rounding, filament tapering, filament bending recovery or a combination thereof. Mixed cleaning elements can be used as well. For example, an elastomeric element may be surrounded by a bristle ring or a circular elastomeric element may be filled with bristle filaments.

The brush head section as disclosed herein provides both, an anchor free mounting of the cleaning elements and an insert formed by a rigid material, either thermoplastic material or metal or metal alloy. The cleaning elements and the insert are over-molded by a thermoplastic material which is able to fasten the cleaning elements and the insert securely. Thus, high precision inserts can be provided representing components which are usable as functional components, such as a coupling element or a mounting area for driving rods. Further, cleaning elements are over-molded to provide a totally closed brush head surface which is highly hygienic and can be cleaned easily.

There is provided a molding device comprising two halves, wherein at least one of the halves is movable. The molding device may be arranged horizontally, meaning that a lower half of the molding device is placed on the ground and an upper half is placed above the lower one. The upper half may be movable up and down to open and to shut the molding device. Alternatively, the molding device may be arranged vertically, meaning that the opening plane of the molding device is arranged substantially perpendicular to the ground. In this embodiment, at least one of the two halves of the molding device may be movable in parallel to the ground to open and to shut the molding device. Alternatively, the opening plane may be arranged in an angle to the ground, wherein the angle is from about 0 to about 90 degree to the ground. In this embodiment, at least one of the two halves of the molding device may be movable on a plane angled to the ground to open and to shut the molding device.

The molding device may comprise at least an over-molding mold cavity. The molding device may comprise two cavities, an insert-molding mold cavity and an over-molding mold cavity, wherein the insert-molding mold cavity and the over-molding mold cavity are arranged in the common opening plane, meaning that the insert-molding and over-molding molding cavity may be opened and closest in the same direction. That means, the insert-molding cavity and the over-molding mold cavity are located adjacent to each other. Insert-molding and/or over-molding mold cavity may be assembled by one or more molding halves and/or one or more slides. Slides may be used to create multi-dimensional surfaces of the molded parts as well as undercuts. In addition, the use of slides also increases geometric variability of the molding device. The molding device may comprise more than one of each molding cavity. One or more insert-molding mold cavities and/or one or more over-molding mold cavities may be comprised in the molding device as described herein. Multiple insert-molding and over-molding mold cavities can be used to produce multiple brush head sections simultaneously.

The molding device further comprises at least one hot runner nozzle connected with the at least one molding cavity. At least one hot runner nozzle may be connected with an insert-molding mold cavity and at least one hot runner nozzle may be connected with an over-molding mold cavity, wherein the at least two hot runner nozzles are located at the same or at opposite sides of the opening plane. It is highly appreciated to use hot runner nozzles for the injection molding to get better injection results and to reduce injection time. Due to geometric reasons, it is further appreciated to locate one of the nozzles at one side of the mold cavities and the other nozzle at the other side of the mold cavities. If more than one nozzle is used per mold cavity the nozzles can be arranged at the same side of the mold cavities. If the molding device has a horizontal opening plane and two mold cavities, the nozzle which is connected to the insert-molding mold cavity may be arranged above the insert-molding mold cavity and the nozzle which is connected to the over-molding mold cavity may be arranged below the over-molding mold cavity. If the molding device has a horizontal opening plane and two mold cavities, the nozzle which is connected to the insert-molding mold cavity may be arranged below the insert-molding mold cavity and the nozzle which is connected to the over-molding mold cavity may be arranged above the over-molding mold cavity. If the molding device has a horizontal opening plane and two mold cavities, both nozzles may be arranged above or below the insert-molding and over-molding mold cavity. If the molding device is arranged vertically so that the opening plane is arranged perpendicular to the ground, the nozzles may be arranged at one or both sides of the molding cavities.

The molding device as disclosed herein further comprises a transferring unit for transferring an insert to the over-molding mold cavity. Said transferring unit may be part of the molding device. For example, said transferring unit may be a rotatable part of the molding device, for example, a rotatable part of the mold cavity, for example a part of the molding halves or a slide, or a rotatable index-plate. The transferring unit may comprise a rotatable index-plate, which is at least rotatable by 180°. Said rotatable part of the molding device may be located at the ejection side of the molding device. If the transferring unit is rotatable, the molding device may comprise a rotation unit for rotating the transferring unit. The molding device as disclosed herein further comprises a holding unit for fixing or arranging the insert in the over-molding mold cavity, so that the insert is arranged partially inside and partially outside of said over-molding mold cavity. Said holding unit may be any suitable grabber, picker, sucker, clamps, clips, squeezers, adhesive element or other component which is able to arrange the insert in a predefined position. In addition, the molding device may comprise another set of holding units for fixing or arranging at least one cleaning element in the over-molding mold cavity, in such that the at least one cleaning element is arranged partially inside and partially outside of said mold cavity. Said second kind of holding units may comprise any suitable grabber, picker, sucker, clamps, clips, squeezers, adhesive element or other component which is suitable to arrange the at least one cleaning element in a predefined position. The holding unit for arranging the at least one cleaning element may be a mold bar. Several mold bars may be combined on a mold bar carrier to a mold bar assembly. The holding unit, for example the mold bar, can be loaded with the cleaning elements outside of the molding device in order to make the manufacturing process more efficient.

In addition, the molding device as disclosed herein may comprise an ejecting unit to eject the resulting brush head section comprising the insert and the at least one cleaning element which are both partially embedded into the molded cleaning element carrier from the molding device. The ejection unit may transfer the mold bar from a position inside and/or under the over-molding mold cavity to a position outside the molding device. Further, the molding device may comprise controlling and/or regulation units for controlling, regulating and/or synchronizing opening and shutting of the insert-molding mold cavity and/or the over-molding mold cavity, injection by the nozzles, transferring of the insert and/or the arrangement of the insert and/or the at least one cleaning element. Suitable controlling and/or regulation units may be computer based. Further, the molding device may comprise conveying and handling systems to convey the insert, the at least one cleaning element and/or any supporting structure, such as holding units to, through and from the molding device.

The molding device comprises more than one insert-molding molding cavity and more than one over-molding cavity so that several brush head sections are injection molded simultaneously. The more than one insert-molding molding cavity and the more than one over-molding mold cavity can be arranged in arrays.

In the following, a detailed description of several example embodiments will be given. It is noted that all features described in the present disclosure, whether they are disclosed in the previous description of more general embodiments or in the following description of example embodiments, even though they may be described in the context of a particular embodiment, are of course meant to be disclosed as individual features that can be combined with all other disclosed features as long as this would not contradict the gist and scope of the present disclosure. In particular, all features disclosed for either one of the method, the device or the brush head section may also be applied to the other one, if applicable.

FIG. 1 shows an example of a molding device 40. The molding device 40 is shown in a side view. The molding device 40 may comprise two halves 42, 44, wherein at least one of the halves 42, 44 may be movable. In one embodiment, the molding device 40 may be arranged horizontally, meaning that a lower half 42 is placed on the ground and an upper half 44 is placed above the lower half 42. Horizontal arrangement may allow an easier transfer of the insert and increases the geometric variability of arranging insert and cleaning elements in the mold cavities. The upper half 44 may be moved up and down in a moving direction $D_M$ to open and to shut the molding device 40.

The molding device 40 comprises at least two mold cavities, namely an insert-molding mold cavity 20 and an over-molding mold cavity 24 which may be arranged adjacent to each other. "Being arranged adjacent to each other" as used herein shall mean that the two mold cavities 20, 24 are located adjacent to each other substantially on the same level inside the molding device 40. An array of several identical cavities, for example 8, 16, 24, 32, 40, 48, 56 or 64 cavities may be used as insert-molding and over-molding mold cavities 20, 24. At least one injection nozzle 22 may be connected to the insert-molding mold cavity 20. In addition, at least one injection nozzle 26 may be connected to the over-molding mold cavity 24. The injection nozzles 22, 26 can be arranged in such that injection into the mold cavities 20, 24 is performed substantially vertically. For example, injection may be performed in direction of gravity and/or against direction of gravity. In addition or alternatively, the injection nozzles 22, 26 may be arranged at opposite sides of the molding cavities 20, 24. The at least one injection nozzle 22 which is connected to the insert-molding mold cavity 20 may be arranged below the mold cavity 20, meaning that the injection nozzle 22 may be located below the plane in which the mold cavities 20, 24 are arranged. Thus, the injection nozzle 22 injects against gravity into the insert-molding mold cavity 20. In addition or alternatively, the at least one injection nozzle 26 which is connected to the over-molding mold cavity 24 may be arranged above the mold cavity 24, meaning that the injection nozzle 26 may be located above the plane in which the mold cavities 20, 24 are arranged. Thus, the injection nozzle 26 injects in the direction of gravity into the over-molding mold cavity 24. Generally applicable to all embodiments, the injection nozzles 22, 26 may be hot runner nozzles or cold runner nozzles. Injection nozzles 22, 26 may be synchronized to each other so that simultaneous injection is possible. In order to regulate and/or synchronize the injection nozzles 22, 26 the molding device 40 may further comprise controlling and/or regulation units.

In the insert-molding mold cavity 20 a thermoplastic material may be injected to form an insert 12. Said insert 12 may be intended to form a part of a brush head of an electric or manual toothbrush. The insert 12 may be a coupling element, a bearing, a part of a bearing or a drive part of a replacement brush head for an electric toothbrush. To form the complex surface of the insert 12 having, for example, protrusions which can be over-molded to form undercuts at least two slides may be used which may be movable in the opening plane of the molding device 40.

In addition, the molding device 40 may comprise a transferring unit 28 which is suitable to transfer the insert 12 from the insert-molding mold cavity 20 to the over-molding mold cavity 24. Thereby, the transferring unit 28 may be rotated, for example by at least 180°. An index-plate being part of the upper half 44 of the molding device 40 may be the transferring unit 28. Said transferring unit 28 may comprise a first holding unit 30 to arrange and/or to fasten the insert 12 to the transferring unit 28. Further, the first holding unit 30 may be suitable to arrange the insert 12 partially inside and partially outside of the over-molding mold cavity 24. In parallel or successively, at least one cleaning element 18 may be arranged partially inside and partially outside of the over-molding mold cavity 24 by a second holding unit 32. A suitable second holding unit 32 may be a mold bar. The transferring unit 28 and the second holding unit 32 may be synchronized, so that the insert 12 is transferred to the over-molding mold cavity 24 while the second holding unit 32 arranges the at least one cleaning element 18 in the over-molding mold cavity 24. To fasten the at least one cleaning element 18 securely in the over-molding mold cavity 24, supporting units 34 may be arranged below the second holding unit 32. "Being arranged below" as used herein shall mean that the supporting unit 34 presses the second holding unit 32 in a direction towards the over-molding mold cavity 24. The second holding unit 32 may seal the mold bar. The mold bar may also be used to form one part of the over-molding mold cavity 24. Further parts of the over-molding mold cavity 24 may be built by at least two slides which may be movable in the opening plane of the molding device 40. Forming the over-molding mold cavity 24 by using a mold bar and slides allows forming cleaning element carriers 16 having a complex surface.

In addition or alternatively, the molding device 40 may further comprise controlling and/or regulation units for controlling, regulating and/or synchronizing the insert-molding and over-molding mold cavities, the injection from the nozzles, the transferring unit and/or the holding units. Opening and shutting of the insert-molding and over-molding mold cavity 20, 24 may be synchronized to the movement of the transferring unit 28 and the holding units 30, 32. For example, transfer of the insert 12 and arranging of the at least one cleaning element 18 is synchronized to occur in parallel. Further, injection into the insert-molding mold cavity 20 and injection into the over-molding mold cavity 24 may be synchronized to happen simultaneously.

In addition or alternatively, the molding device 40 may further comprise an ejection unit 36 which ejects the resulting brush head section 10 from the over-molding mold cavity 24. All features, whether described individually or in combination with respect to FIGS. 2 and 3, are also applicable to the molding device 40 shown in FIG. 1.

The molding process shall be explained exemplary. If the molding device 44 opens, the inserts 12 are attached to the first holding unit 30 on that side of the index-plate 28 which was in contact to the insert-molding mold cavity 20. The other side of the index-plate 28 which was in contact to the over-molding mold cavity 24 does not contain any inserts 12, because the inserts 12 are released from the first holding unit 30 during ejection of the brush head section 10 from the over-molding mold cavity 24. Then, the index-plate 28 rotates by 180° and the inserts 12 are arranged above the over-molding mold cavity 24. If the molding device 40 closes now, the inserts 12 are partially located in the over-molding mold cavity 24 to be over-molded. Thermoplastics are injected into both molding cavities 20, 24, thereby the insert 12 is formed in the insert-molding mold cavity 20 being attached to the first holding unit 30, and the cleaning element carrier 16 is formed in the over-molding mold cavity 24 over-molding the insert 12 and the cleaning elements 18. During opening of the molding device 40 the first holding unit 30 releases the brush head section 10. Then, the brush head section 10 can be removed from the molding device 40 while staying in the second holding unit 32.

FIGS. 2A and 2B show a top view of the upper half 44 of the molding device 40 as shown in FIG. 1. All features disclosed in FIG. 1, whether described individually or in combination and which relate to the upper half 44, are also applicable to the upper half 44 shown in FIG. 2. Features that are in common with the molding device 40 shown in FIG. 1 are designated with the same reference numerals. The upper half 44 is shown from the inner side of the molding device 40. The "inner side" as used herein shall mean the side of the upper half 44 which is directed towards the lower half 42. The insert-molding mold cavity 20 is shown on the left and the over-molding mold cavity 24 is shown on the right of FIGS. 2A and 2B. However, mold cavities 20, 24 may be arranged the other way round. The upper half 44 may carry a transfer unit 28, which might be an index-plate. Said index-plate 28 may be rotatable at least by 180°. First holding units 30 may be attached to the index-plate 28, wherein the holding units 30 are able to carry the inserts 12, the latter being molded in the insert-molding mold cavity 20 (not shown). FIG. 2A shows the upper half 44 after the first injection molding step in the insert-molding mold cavity 20 when the inserts 12 are attached to the first holding unit 30 on that side of the index-plate which was in contact to the insert-molding mold cavity 20. The other side of the index-plate 28 which was in contact to the over-molding mold cavity 24 does not contain any molded component because the resulting brush head section 10 was released after the injection molding step. FIG. 2B shows the index-plate 28 after rotations by 180° so that the inserts 12 are now arranged above the over-molding mold cavity 24. If thermoplastics are now injected into both molding cavities 20, 24, the insert 12 is formed in the insert-molding mold cavity 20 being attached to the first holding unit 30 and the cleaning element carrier 16 is formed in the over-molding mold cavity 24.

Figure 3:
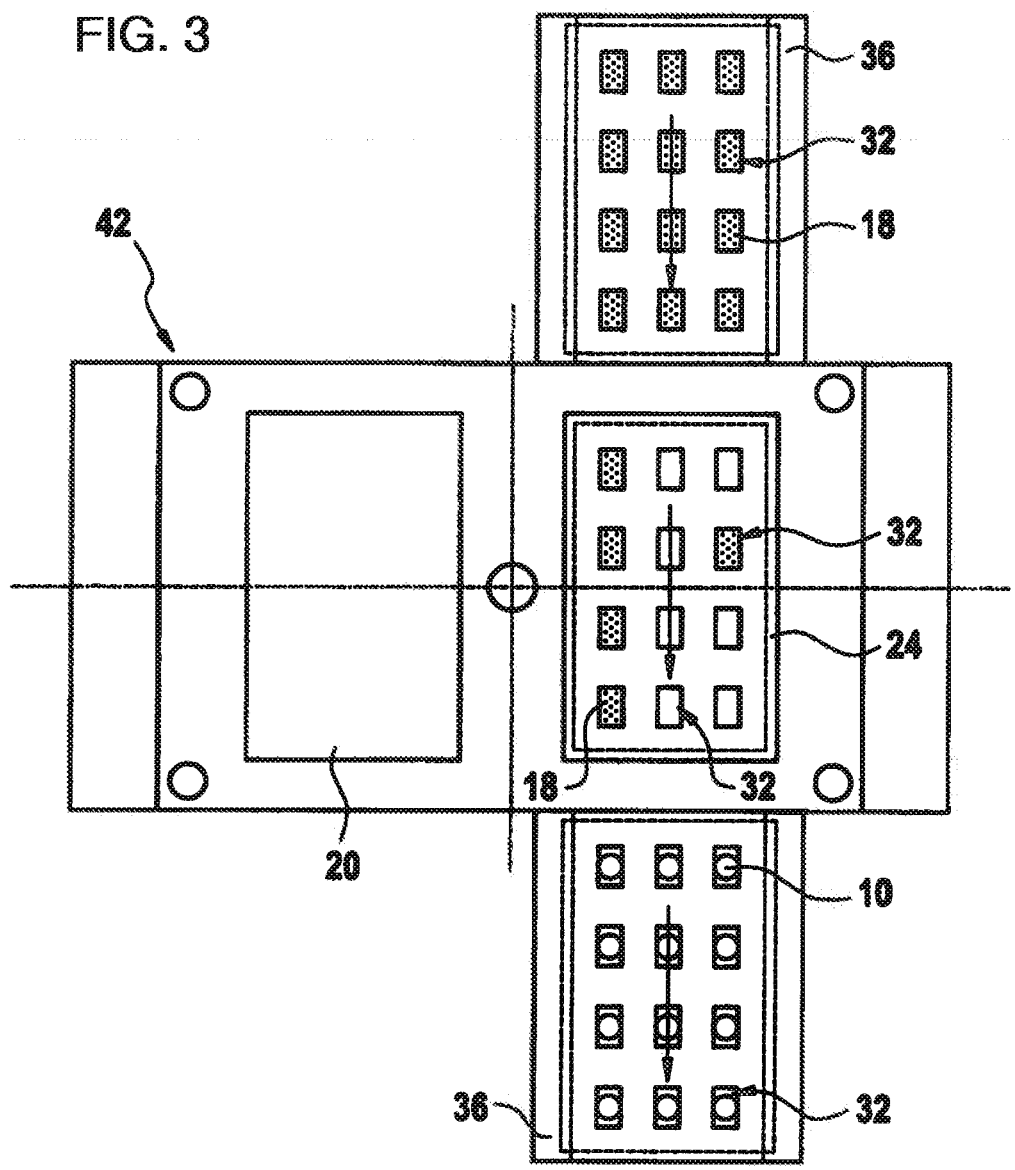
FIG. 3 shows a top view of the inner side of the lower half 42 of the molding device 40.

FIG. 3 shows a top view of the lower half 42 of the molding device 40 as shown in FIG. 1. All features disclosed in FIG. 1, whether described individually or in combination and which relate to the lower half 42, are also applicable to the lower half shown in FIG. 3. Features that are in common with the molding device 40 shown in FIG. 1 are designated with the same reference numerals. The lower half 42 is shown from the inner side of the molding device 40. The "inner side" as used herein shall mean the side of the lower half 42 which is directed towards the upper half 44. The insert-molding mold cavity 20 is shown on the left side and the over-molding mold cavity 24 is shown on the right of FIG. 3. However, mold cavities 20, 24 may be arranged the other way round. A second holding unit 32 which might be suitable to carry at least one cleaning element 18 is arranged below the over-molding mold cavity 24. The second holding unit 32 may be a mold bar.

Several second holding units 32 may be arranged on a holding unit carrier so that several second holding units 32 can be located simultaneously in the over-molding mold cavity 24. The second holding unit 32 may be introduced into the molding device 40 from one side and ejected from the molding device 40 at the other side. Introducing and ejecting of the second holding units 32 at different sides of the molding device 40 allows an automatic transportation of the second holding units 32 through the molding device 40. Automatic transportation may increase manufacturing speed of the brush head section 10. For automatic transportation, the molding device 40 may comprise conveying and handling systems to convey the insert, the at least one cleaning element and/or any supporting structure, such as the holding unit 32 to, through and from the molding device. The at least one cleaning element 18 may be put into the second holding unit 32 outside the molding device 40, may remain in the second holding unit 32 during injection molding inside the molding device 40 and may also remain in the second holding unit 32 during ejection from the molding device 40 using the conveying system. Thus, the resulting brush head section 10 is carried by the second holding units 32 outside the molding device 40 and can be transferred by the conveying system to further manufacturing steps.

Figure 4:
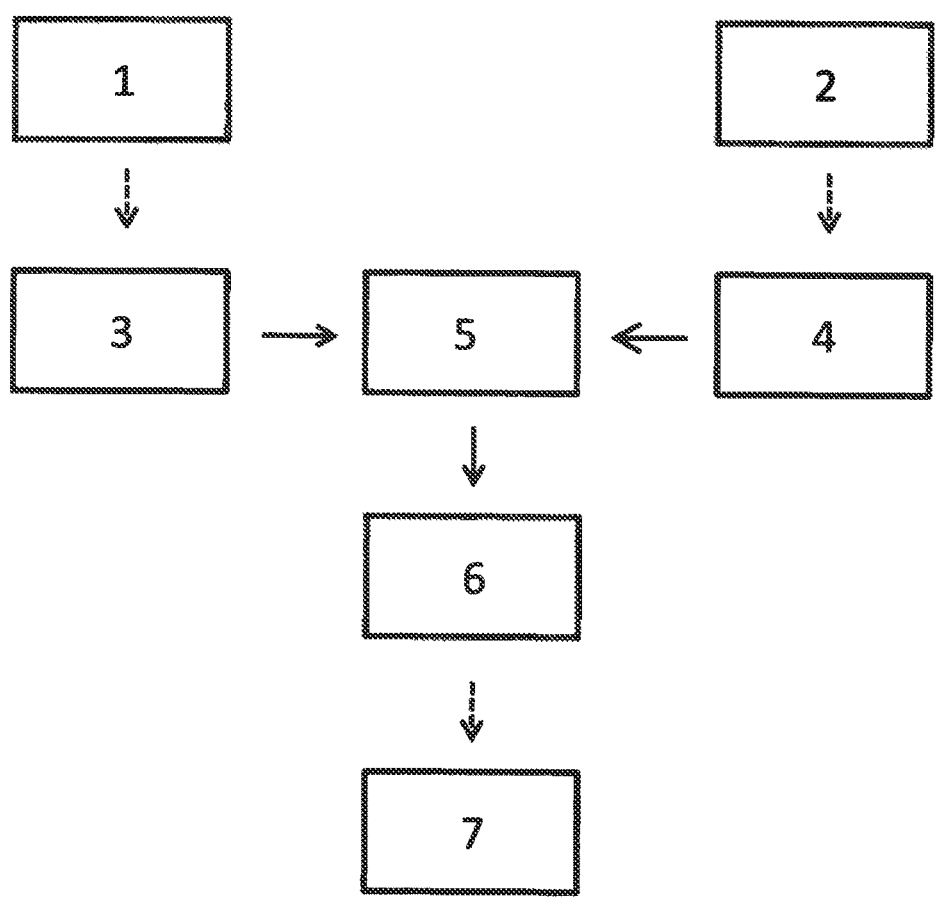
FIG. 4 shows a flow-chart showing the manufacturing process schematically.

FIG. 4 shows a flow chart exemplifying the molding process schematically. In step 1 the insert 12 may be formed by injection molding in the insert-molding mold cavity 20. Step 3 provides the insert 12 into the over-molding mold cavity 24 for example, using the index-plate 28. As shown by the dashed line step 1 is optional. In parallel (step 2) at least one cleaning element 18 is placed into the second holding unit 32 forming a cleaning element pattern. After positioning the at least one cleaning element 18, the second holding unit 32 is transferred to the over-molding mold cavity 24 (step 4). As shown by the dashed line step 2 is optional, meaning that the at least one cleaning element 18 can also be provided differently only performing step 4. Step 5 represents the manufacturing of the brush head section 10 by over-molding the insert 12 and the at least one cleaning element 18. Finally, the brush head section 10 is ejected from the over-molding mold cavity 24 (step 6). Optionally, the brush head section 10 may be further processed in an additional step 7, for example, by adding additional cleaning elements 18'.

Figure 5:
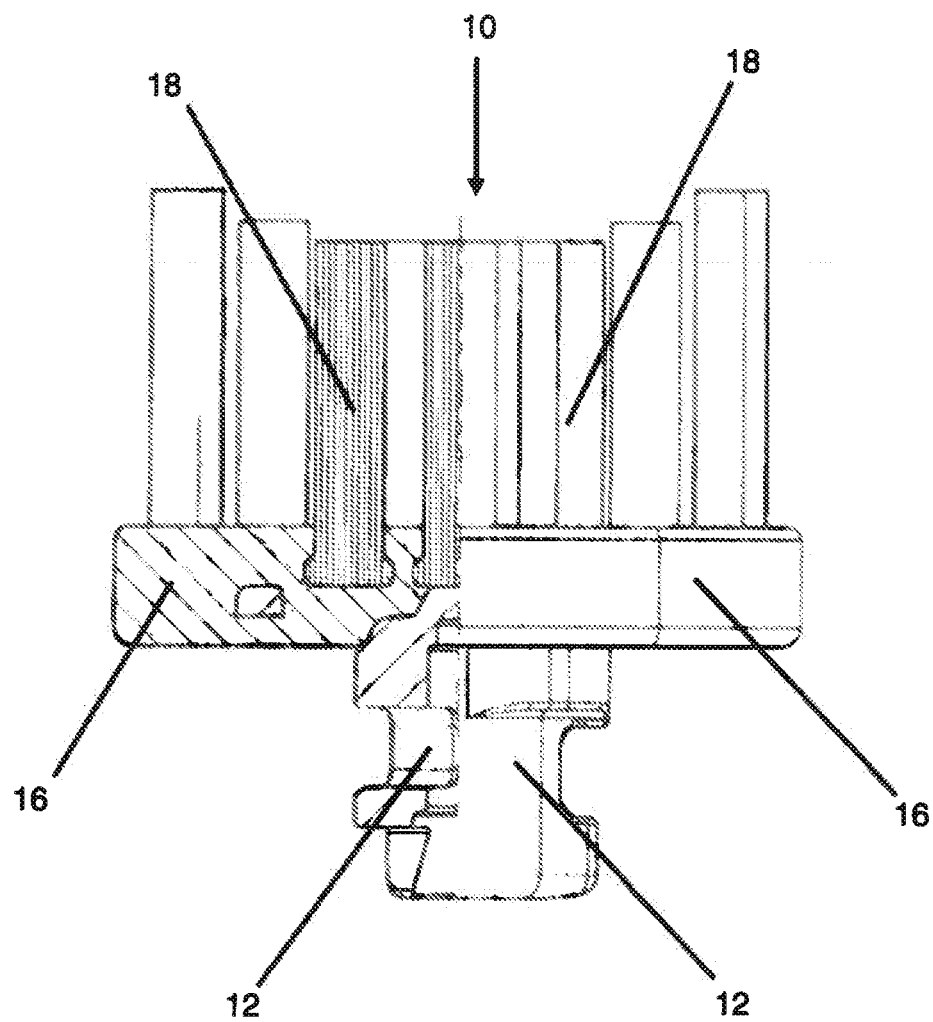
FIG. 5 shows a bush head section 10 having an insert 12, at least one cleaning element 18 and a cleaning element carrier 16 partially embedding the insert 12 and the at least one cleaning element 18.

A brush head section 10 is produced using, for example, the method disclosed before. An example of a brush head section 10 is shown in FIG. 5. A sectional drawing of the brush head section 10 is shown on the left side and a side view of the brush head section 10 is shown on the right side of FIG. 5. An insert 12 is partially embedded in a cleaning element carrier 16. The insert 12 may comprise at least one protrusion to form an undercut after being over-molded by the material of the cleaning element carrier 16. Having one or more undercuts, the insert 12 is securely fastened inside the cleaning element carrier 16 by positive-fit. The cleaning element carrier 16 may be a disk. At one side of the cleaning element carrier 16, part of the insert 12 protrudes and at the other side of the cleaning element carrier 16 one or more cleaning elements 18 protrude being partially embedded into the material of the cleaning element carrier 16. Insert 12 and cleaning element carrier 16 may be formed by injection molding of thermoplastics, wherein the insert 12 is molded first. During the over-molding step one end of the one or more cleaning elements 18 and a part of the insert 12 are partially over-molded by the material of the cleaning element carrier 16. The insert 12 may be formed by a first thermoplastic material having a higher hardness than the second thermoplastic material from which the cleaning element carrier 16 is formed. In addition or alternatively, the first thermoplastic material used to form the insert 12 may have a higher melting point, strength, rigidity, abrasion resistance and/or heat resistance and/or can be injected with a higher pressure than the second thermoplastic material used to form the cleaning element carrier 16. In addition or alternatively, the first thermoplastic material used to form the insert 12 may have a lower viscosity in molten state than the second thermoplastic material used to form the cleaning element carrier 16. The first thermoplastic material which may be used to injection mold the insert 12 may be polyoxymethylene. The second thermoplastic material which may be used to over-mold the insert and the at least one cleaning element 18 which forms the cleaning element carrier 16 may be polypropylene, polyethylene, polyethylene terephthalate, or a mixture thereof. The insert 12 may be a part of a replacement brush head to be used in an electric toothbrush or a part of a manual toothbrush. Suitable parts of a replacement brush head which may be formed as an insert 12 as disclosed herein are, for example, a coupling element, a part of a bearing, a bearing or a drive connectable to a driving shaft. Suitable parts of a manual toothbrush which may be formed as an insert 12 as disclosed herein are the brush head, a tongue cleaner or polishing element or a part of the neck or a part of the handle. The cleaning element 18 as disclosed herein may be an elastomeric element, such as for example, elastomeric walls, elastomeric bars, elastomeric gutters, elastomeric curves, elastomeric circles, textured elements, elastomeric nubs, elastomeric fins, elastomeric pins polishing elements, such as, for example, polishing cups or a combination thereof or one or more bristle filaments, or a combination thereof. The cleaning elements 18 may be arranged in a predefined pattern. A "pattern" as used herein shall include every arrangement of one or more kinds of cleaning elements 18 as well as different angles of inclination relative to the vertical, different horizontal profiles, or a combination thereof.

Figure 6:
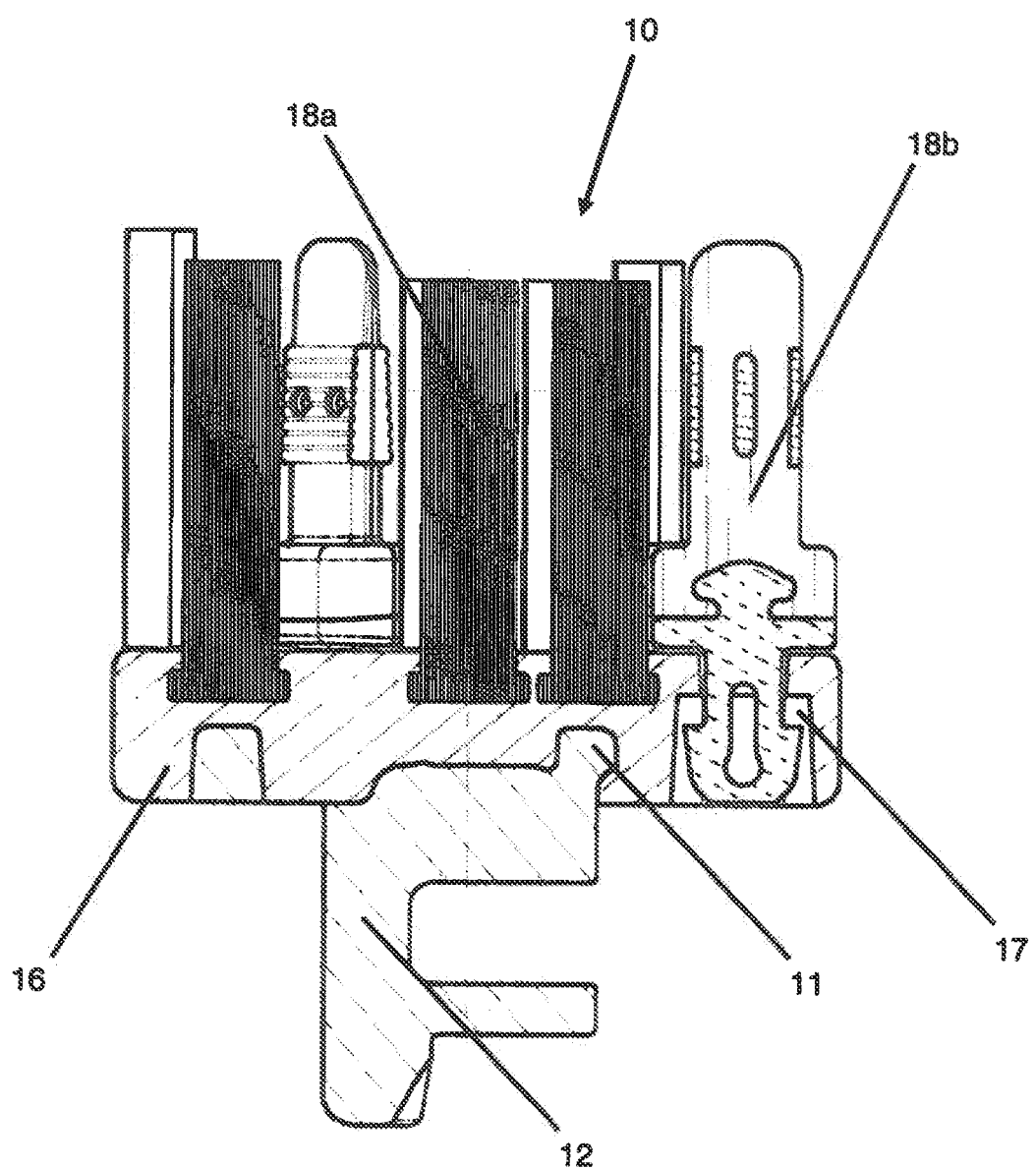
FIG. 6 shows a brush head section 10 having two types of cleaning elements 18, namely a bristle tuft 18a and an elastomeric element 18b.

FIG. 6 shows another example of a brush head section 10 as disclosed herein. All features disclosed in FIG. 5, whether described individually or in combination, are also applicable to the brush head section 10 shown in FIG. 6. Features that are in common with the brush head section 10 shown in FIG. 5 are designated with the same reference numerals. An insert 12 is shown having at least one undercut 11. The undercut 11 is formed as a protrusion which is over-molded during the over-molding step. Thereby, the undercut 11 is formed which fastens the insert 12 into the cleaning element carrier 16. The protrusion may be a circumferential bulge. Cleaning element 18a may be a bristle, a plurality of bristles or a bristle tuft which is partially embedded into the cleaning element carrier 16. Cleaning element 18a may be used together with cleaning elements 18b being an elastomeric element. The elastomeric cleaning element 18b can be over-molded or mounted into a recess 17 formed in the cleaning element carrier 16. The elastomeric cleaning element 18b may be clipped into the recess 17, wherein the recess 17 comprises at least one undercut to fasten the elastomeric cleaning element 18b securely. The elastomeric cleaning element 18b may be intended to vibrate or to move relative to the cleaning element carrier 16 to achieve additional cleaning effects.

To form the recess 17 the insert 12 may be molded together with place holder elements 14. FIGS. 7A and 7B show an example of a cleaning element carrier 16 having such place holder elements 14. All features disclosed in FIG. 5 or 6, whether described individually or in combination, are also applicable to the cleaning element carrier 16 shown in FIGS. 7A and 7B. Features that are in common with the brush head section 10 shown in FIGS. 5 and 6 are designated with the same reference numerals. In FIGS. 7A and 7B, cleaning elements 18 are not shown, but every cleaning element 18 may be partially embedded into the cleaning element carrier 16 in every arrangement. Place holder elements 14 may be formed together with the insert 12 and may be over-molded by the material of the cleaning element carrier 16 (FIG. 7A). Place holder elements 14 are intended to be punched out after formation of the cleaning element carrier 16. Thus, undercuts can be produced to mount cleaning elements 18 movable into the recesses 17 left in the cleaning element carrier 16. If the place holder elements 14 are located adjacent to the insert 12, they can be molded as protrusions having a predetermined breaking point. A predetermined breaking point may be realized by combining two thermoplastics which do not aggregate. In addition or alternatively, place holder elements 14 can be spaced from the insert 12. Thereby, a small bridging bar 13 may combine the insert 12 and the place holder element 14. After being over-molded, the small bridging bar 13 is punched out together with the place holder element 14 exposing the recess 17 in the cleaning element carrier 16. Therefore, the thermoplastics used should show less adhesion to each other and should not aggregate.

FIG. 7B shows the cleaning element carrier 16 after punching out of the place holder element 14. A plunger 15 is placed above the place holder element 14 in the cleaning element carrier 16. If the plunger 15 is moved towards the place holder element 14, the place holder element 14 is removed from the cleaning element carrier 16 exposing the recess 17. The recess 17 may be a through-hole through the cleaning element carrier 16. One of the openings of the through-hole may be smaller than the opening at the other side of the cleaning element carrier 16 so that undercuts are formed. The smaller opening may be arranged at that surface of the cleaning element carrier 16 which is intended to carry cleaning elements 18. Movable cleaning elements 18 may be mounted to the recess 17. After mounting the movable cleaning elements 18 show a high retention force due to undercuts formed in the cleaning element carrier 16.

FIGS. 8A and 8B show another example of a brush head section 10 as disclosed herein. All features disclosed in FIGS. 5 to 7, whether described individually or in combination, are also applicable to the brush head section 10 shown in FIG. 8. Features that are in common with the brush head section 10 shown before are designated with the same reference numerals. FIG. 8A shows the brush head section 10 comprising an insert 12 and a cleaning element 18c which are both partially embedded in the cleaning element carrier 16. FIG. 8B shows the brush head section 10 comprising an insert 12 and two different cleaning elements 18a and 18c which all are partially embedded in the cleaning element carrier 16. Two different types of cleaning elements 18 are shown, but the brush head section 10 can also comprise further types of cleaning elements. Cleaning element 18a may be a bristle, a plurality of bristles or a bristle tuft which is partially embedded into the cleaning element carrier 16. Cleaning element 18a may be used alone or together with a cleaning element 18c being an elastomeric element. The elastomeric cleaning element 18c is placed in the centre of the cleaning element carrier 16. The elastomeric cleaning element 18c may be a cup structure which may have separating plates which divide the inside space of the cup into two or more subspaces. The separating plates may be also partial plates. The elastomeric cleaning element 18c can be fixed to the cleaning element carrier 16 by mounting it into a recess formed in the cleaning element carrier 16. The elastomeric cleaning element 18c may be clipped into a recess, wherein the recess may comprise at least one undercut to fasten the elastomeric cleaning element 18c securely. Alternatively, the elastomeric cleaning element 18c can be fixed to the cleaning element carrier 16 by over-molding. In such an embodiment, the cleaning element 18c may comprise a recess so that a protrusion 19 consisting of the over-molding material is formed during over-molding. The recess in the cleaning element 18c may comprise at least one undercut to fasten the elastomeric cleaning element 18c securely via the protrusion 19. The material of the cleaning element 18c may be combinable with the material of the cleaning element carrier 16 so that the cleaning element 18c and the cleaning element carrier 16 are joined integrally by material engagement. The elastomeric cleaning element 18c may be intended to carry a cleaning material, for example, toothpaste to achieve additional cleaning effects, for example, polishing effects.

FIGS. 8A and 8B in particular show that the insert 12 has a disc-like section that has a diameter that is generally larger than the more cylinder-like coupling part which had been arranged outside of the over-molding mold cavity in the manufacturing process. The cleaning element carrier 16 in this example embodiment engages behind this disc-like section of the insert 12, in particular the cleaning element carrier 16 may engage behind the disc-like section along the full circumference of the disc-like section. In other embodiments, the cleaning element carrier may only partly engage behind the disc-like section. In some embodiments, the insert may have one or more radially protruding projection behind which the cleaning element carrier engages. The effect of this engaging behind structure is that a chemical bond between the insert 12 and the cleaning element carrier is not required and that these two components are non-detachably connected even in cases where the first and the second thermoplastic materials from which the insert and the cleaning element carrier, respectively, are manufactured are not compatible which each other, i.e. where the first and second thermoplastic material do not chemically bond which each other in the over-molding process.

FIG. 9 shows another example of a brush head section 10 as disclosed herein. All features disclosed in FIGS. 5 to 8, whether described individually or in combination, are also applicable to the brush head section 10 shown in FIG. 9. Features that are in common with the brush head section 10 shown before are designated with the same reference numerals. An insert 12 is shown being a drive part, a bearing shaft, a carrier spindle or a security anchor. Said insert 12 may be made from a metal or a metal alloy, for example, the insert 12 may be made from stainless steel. The insert 12 is over-molded with a thermoplastic, for example, polypropylene, polyethylene or polyethylene terephthalate, wherein the cleaning element carrier 16 is formed. In parallel to the over-molding of the insert 12, cleaning elements 18 are over-molded at the opposite side of the cleaning element carrier 16 bulge. The cleaning elements 18 may be a plurality of bristles, a bristle tuft or an elastomeric element.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for producing a brush head section for an oral care device comprising the steps of:
   injecting a first thermoplastic material into an insert-forming mold cavity to form an insert;
   transferring said insert into an over-molding mold cavity, wherein the insert is arranged partially inside and partially outside of said over-molding mold cavity;
   arranging one end of at least one cleaning element in said over-molding mold cavity, wherein the at least one cleaning element is arranged partially inside and partially outside of said over-molding mold cavity and wherein the at least one cleaning element is arranged within a mold bar in that the ends of the at least one cleaning element intended to clean are located inside the mold bar and the ends intended to be mounted into the brush head protrudes from the mold bar;
   injecting a second thermoplastic material into said over-molding mold cavity so that the part of the insert and the part of the at least one cleaning element which are located inside said over-molding mold cavity are over-molded by the second thermoplastic material, which second thermoplastic material thereby forms a cleaning element carrier, wherein the insert has a section behind which the cleaning element carrier engages the insert, wherein the insert comprises a coupling element or a part of a driving system of the oral care device, and wherein the hardness of the second thermoplastic material is smaller than the hardness of the first thermoplastic material; and
   ejecting the resulting brush head section from said over-molding mold cavity, wherein the brush head section remains in the mold bar.

2. The method according to claim 1, wherein the step of injecting a thermoplastic into the insert-forming mold cavity and/or the over-molding mold cavity is a hot runner injection.

3. The method according to claim 1 or 2, wherein the steps of injecting the first thermoplastic material into the insert forming mold cavity and injecting the second thermoplastic material into the over-molding mold cavity are performed substantially simultaneously.

4. The method according to claim 1, wherein the transfer of the insert into the over-molding mold cavity comprises rotating an index-plate horizontally.

5. The method according to claim 1, wherein the at least one cleaning element comprises an elastomeric material which is injected into the mold bar.

6. The method according to claim 1, wherein the steps of transferring the insert and arranging one end of the at least one cleaning element are performed substantially simultaneously.

7. The method according to claim 1, comprising injection-molding at least one elastomeric element onto the brush head section.

8. A brush head section for an oral care device comprising an insert comprising a replacement brush head and made from a first thermoplastic material by injection-molding, at least one oral cleaning element and a cleaning element carrier consisting of a second thermoplastic material or a second thermoplastic mixture, wherein the insert and the at least one cleaning element are partially embedded into said cleaning element carrier by over-molding, wherein the insert comprises a substantially flat disc having a protrusion at one side thereof, the disc being overmolded so that only the protrusion protrudes from the cleaning element carrier after overmolding, and wherein the hardness of the second thermoplastic material is smaller than the hardness of the first thermoplastic material.

9. The brush head section according to claim 8, wherein the insert comprises a second insert which has been over-molded at least partially by the second thermoplastic material to form an at least two component insert.

10. The brush head section according to claim 9, wherein the second insert consists of a metal or a metal alloy.

11. The brush head section according to claim 8, wherein the insert is selected from the group consisting of, a coupling element connectable to a driving shaft or a drive part, a part of a bearing, a bearing or a bearing shaft, and a carrier spindle or a security anchor.

12. The brush head section according to claim 11, wherein the insert comprising a substantially flat disc has a section behind which the cleaning element carrier engages and a coupling part which is connectable to a bearing.

13. The brush head section according to claim 8, wherein the at least one cleaning element is a bristle tuft comprising at least one bristle filament or an elastomeric element selected from the group consisting of an elastomeric wall, an elastomeric bar, an elastomeric gutter, an elastomeric curve, an elastomeric circle, a textured element, an elastomeric nub, an elastomeric fin, an elastomeric pin, a polishing element, a polishing cup, and any a combination thereof.

14. The brush head section according to claim 8, wherein the insert comprises a part of a manual toothbrush.

15. A molding device comprising
at least one insert-molding mold cavity, and at least one over-molding mold cavity, wherein the at least one insert-molding mold cavity and the at least one over-molding mold cavity have a common opening plane and a transferring unit for transferring an insert molded in said insert-molding mold cavity to said over-molding mold cavity, comprising an index-plate suitable to be rotated by at least 180° and a rotation unit for rotating the index-plate;
at least one hot runner nozzle connected to said at least one over-molding mold cavity;
a first holding unit for fixing an insert in each of the at least one over-molding mold cavity;
a second holding unit being a mold bar for fixing at least one cleaning element in each of the at least one over-molding mold cavity; and
an ejecting unit to eject a molded brush head section from the molding device, wherein the ejection unit is structured to transfer the mold bar from a position inside and/or under the overmolding mold cavity to a position outside the molding device.

* * * * *